United States Patent
Rybolt et al.

(10) Patent No.: US 9,237,953 B2
(45) Date of Patent: Jan. 19, 2016

(54) MECHANICAL ASSEMBLY OF PEGS TO PROSTHESIS

(71) Applicant: DEPUY (IRELAND), Cork (IE)

(72) Inventors: Jeffrey A Rybolt, Fort Wayne, IN (US); Bryan J Smith, Fort Wayne, IN (US)

(73) Assignee: DEPUY (IRELAND), Cork (IE)

( * ) Notice: Subject to any disclaimer, the term of this patent is extended or adjusted under 35 U.S.C. 154(b) by 9 days.

(21) Appl. No.: 14/186,394

(22) Filed: Feb. 21, 2014

(65) Prior Publication Data

US 2014/0277547 A1    Sep. 18, 2014

Related U.S. Application Data

(60) Provisional application No. 61/799,570, filed on Mar. 15, 2013.

(51) Int. Cl.
*A61F 2/38*    (2006.01)
*A61F 2/30*    (2006.01)

(52) U.S. Cl.
CPC . *A61F 2/389* (2013.01); *A61F 2/38* (2013.01); *A61F 2/30767* (2013.01); *A61F 2/30907* (2013.01); *A61F 2/3859* (2013.01); *A61F 2002/30011* (2013.01); *Y10T 29/49861* (2015.01); *Y10T 29/49888* (2015.01)

(58) Field of Classification Search
CPC .......... A61F 2/34–2/38; A61F 1/3804; A61F 2/3859; A61F 2/3868; A61F 2/389; A61F 2002/30011; A61F 2/30767
USPC .......... 623/20.34, 20.14–20.17, 20.26–20.33
See application file for complete search history.

(56) References Cited

U.S. PATENT DOCUMENTS

| | | | | |
|---|---|---|---|---|
| 4,479,271 A | * | 10/1984 | Bolesky et al. | 623/20.17 |
| 4,923,473 A | * | 5/1990 | Griss et al. | 623/22.38 |
| 4,938,769 A | * | 7/1990 | Shaw | 623/20.15 |
| 4,955,919 A | * | 9/1990 | Pappas et al. | 623/22.26 |
| 5,104,410 A | | 4/1992 | Chowdhary | |
| 5,198,308 A | | 3/1993 | Shetty | |
| 5,226,917 A | * | 7/1993 | Schryver | 623/22.37 |
| 5,282,861 A | | 2/1994 | Kaplan | |
| 5,310,408 A | * | 5/1994 | Schryver et al. | 623/22.37 |
| 5,360,452 A | * | 11/1994 | Engelhardt et al. | 623/22.37 |
| 5,534,027 A | * | 7/1996 | Hodorek | 128/898 |
| 5,534,032 A | * | 7/1996 | Hodorek | 623/20.32 |
| 5,549,691 A | * | 8/1996 | Harwin | 623/22.37 |
| 5,571,198 A | * | 11/1996 | Drucker et al. | 623/22.34 |
| 5,609,648 A | * | 3/1997 | Oehy et al. | 623/22.19 |
| 5,645,606 A | * | 7/1997 | Oehy et al. | 623/22.34 |
| 5,702,475 A | * | 12/1997 | Zahedi | 623/22.21 |
| 5,725,580 A | * | 3/1998 | Cloutier et al. | 623/16.11 |
| 5,725,588 A | * | 3/1998 | Errico et al. | 623/22.36 |
| 5,728,748 A | | 3/1998 | Sun | |
| 5,876,456 A | * | 3/1999 | Sederholm et al. | 623/16.11 |
| 5,879,389 A | * | 3/1999 | Koshino | 623/20.11 |
| 5,879,398 A | * | 3/1999 | Swarts et al. | 623/22.21 |
| 5,879,400 A | | 3/1999 | Merrill | |
| 5,888,205 A | * | 3/1999 | Pratt et al. | 623/22.35 |
| 5,911,758 A | * | 6/1999 | Oehy et al. | 623/20.32 |
| 5,925,077 A | * | 7/1999 | Williamson et al. | 623/22.34 |
| 6,017,975 A | | 1/2000 | Saum | |

(Continued)

*Primary Examiner* — Alvin Stewart

(57) ABSTRACT

An orthopaedic prosthesis for cementless fixation has a solid metal base and porous metal pegs extending out from the base. The pegs are mechanically, rather than metallurgically, fixed to the base. A process for making such a prosthesis is also disclosed.

43 Claims, 9 Drawing Sheets

(56) References Cited

U.S. PATENT DOCUMENTS

| | | | |
|---|---|---|---|
| 6,120,541 A * | 9/2000 | Johnson | 623/14.12 |
| 6,120,546 A * | 9/2000 | Dye et al. | 623/22.34 |
| 6,152,962 A * | 11/2000 | DeCarlo, Jr. | 623/22.34 |
| 6,206,881 B1 * | 3/2001 | Frigg et al. | 606/291 |
| 6,228,900 B1 | 5/2001 | Shen | |
| 6,242,507 B1 | 6/2001 | Saum | |
| 6,245,276 B1 | 6/2001 | McNulty | |
| 6,281,264 B1 | 8/2001 | Salovey | |
| 6,316,158 B1 | 11/2001 | Saum | |
| 6,319,285 B1 * | 11/2001 | Chamier et al. | 623/22.32 |
| 6,945,448 B2 | 9/2005 | Medlin | |
| 7,189,262 B2 * | 3/2007 | Hayes et al. | 623/20.32 |
| 7,294,149 B2 * | 11/2007 | Hozack et al. | 623/20.34 |
| 7,524,325 B2 * | 4/2009 | Khalili | 606/290 |
| 7,628,818 B2 | 12/2009 | Hazebrouck | |
| 7,988,736 B2 * | 8/2011 | May et al. | 623/20.17 |
| 8,066,770 B2 | 11/2011 | Rivard | |
| 8,105,367 B2 * | 1/2012 | Austin et al. | 606/280 |
| 8,187,335 B2 | 5/2012 | Wyss | |
| 8,192,498 B2 | 6/2012 | Wagner | |
| 8,206,451 B2 | 6/2012 | Wyss | |
| 8,236,061 B2 | 8/2012 | Heldreth | |
| 8,470,047 B2 | 6/2013 | Hazebrouck | |
| 8,556,985 B2 * | 10/2013 | Meridew | 623/22.36 |
| 8,632,600 B2 * | 1/2014 | Zannis et al. | 623/20.17 |
| 8,658,710 B2 | 2/2014 | McKellop | |
| 8,715,359 B2 * | 5/2014 | Deffenbaugh et al. | 623/20.29 |
| 8,900,321 B2 * | 12/2014 | Weiss et al. | 623/22.35 |
| 2002/0161448 A1 * | 10/2002 | Hayes et al. | 623/20.32 |
| 2003/0014122 A1 * | 1/2003 | Whiteside | 623/20.32 |
| 2003/0212161 A1 | 11/2003 | McKellop | |
| 2005/0125068 A1 * | 6/2005 | Hozack et al. | 623/20.32 |
| 2006/0257358 A1 | 11/2006 | Wen | |
| 2007/0142921 A1 * | 6/2007 | Lewis et al. | 623/22.36 |
| 2007/0173948 A1 * | 7/2007 | Meridew et al. | 623/22.24 |
| 2007/0219637 A1 * | 9/2007 | Berelsman et al. | 623/19.11 |
| 2008/0046091 A1 * | 2/2008 | Weiss et al. | 623/22.37 |
| 2008/0199720 A1 | 8/2008 | Liu | |
| 2009/0011384 A1 * | 1/2009 | Collins et al. | 433/174 |
| 2009/0018560 A1 * | 1/2009 | Mayer et al. | 606/151 |
| 2009/0210067 A1 * | 8/2009 | Meridew | 623/22.24 |
| 2009/0292365 A1 | 11/2009 | Smith | |
| 2009/0326666 A1 | 12/2009 | Wyss | |
| 2009/0326667 A1 | 12/2009 | Williams | |
| 2009/0326674 A1 | 12/2009 | Liu | |
| 2010/0057217 A1 * | 3/2010 | Breimesser et al. | 623/22.34 |
| 2010/0094420 A1 * | 4/2010 | Grohowski, Jr. | 623/16.11 |
| 2010/0098574 A1 | 4/2010 | Liu | |
| 2010/0145393 A1 * | 6/2010 | Fallin et al. | 606/301 |
| 2010/0256771 A1 * | 10/2010 | Roberts et al. | 623/22.36 |
| 2011/0029092 A1 | 2/2011 | Deruntz | |
| 2011/0035013 A1 * | 2/2011 | Winslow et al. | 623/19.13 |
| 2011/0035017 A1 | 2/2011 | Deffenbaugh | |
| 2012/0067853 A1 | 3/2012 | Wang | |
| 2013/0022943 A1 * | 1/2013 | Collins et al. | 433/174 |
| 2013/0066437 A1 * | 3/2013 | Weeden | 623/22.36 |
| 2013/0218284 A1 * | 8/2013 | Eickmann et al. | 623/20.34 |
| 2013/0310945 A1 * | 11/2013 | Slone et al. | 623/22.34 |
| 2014/0277517 A1 * | 9/2014 | Winslow | 623/19.11 |
| 2014/0277544 A1 * | 9/2014 | Viscogliosi et al. | 623/20.32 |

* cited by examiner

MECHANICAL ASSEMBLY OF PEGS TO PROSTHESIS

CROSS REFERENCE TO RELATED APPLICATION

This application claims priority to U.S. Prov. App. No. 61/799,570 filed Mar. 15, 2013, entitled "Mechanical Assembly of Pegs to Prosthesis," which is incorporated by reference herein in its entirety.

TECHNICAL FIELD

The present disclosure relates generally to an implantable orthopaedic prosthesis, and more particularly to an implantable prosthesis having a bearing component and another component supporting the bearing component.

BACKGROUND

During the lifetime of a patient, it may be necessary to perform a joint replacement procedure on the patient as a result of, for example, disease or trauma. The joint replacement procedure may involve the use of a prosthesis that is implanted into one or more of the patient's bones. In the case of a knee replacement procedure, a tibial tray is implanted into the patient's tibia. A bearing is then secured to the tibial tray. The condyle surfaces of a replacement femoral component bear against the tibial bearing.

One type of knee prosthesis is a fixed-bearing knee prosthesis. As its name suggests, the bearing of a fixed-bearing knee prosthesis does not move relative to the tibial tray. Fixed-bearing designs are commonly used when the condition of the patient's soft tissue (i.e., knee ligaments) does not allow for the use of a knee prosthesis having a mobile bearing.

In contrast, in a mobile-bearing type of knee prosthesis, the bearing can move relative to the tibial tray. Mobile-bearing knee prostheses include so-called "rotating platform" knee prostheses, wherein the bearing can rotate about a longitudinal axis on the tibial tray.

Tibial trays are commonly made of a biocompatible metal, such as a cobalt chrome alloy or a titanium alloy.

For both fixed and mobile-bearing knee prostheses, the tibial trays may be designed to be cemented into place on the patient's tibia or alternatively may be designed for cementless fixation. Cemented fixation relies on mechanical bonds between the tibial tray and the cement as well as between the cement and the bone. Cementless implants generally have surface features that are conducive to bone ingrowth into the implant component and rely to a substantial part on this bony ingrowth for secondary fixation; primary fixation is achieved through the mechanical fit of the implant and the prepared bone.

Tibial components of both fixed and mobile-bearing and cemented and cementless knee arthroplasty systems are commonly modular components, comprising a tibial tray and a polymeric bearing carried by the tibial tray. The tibial trays commonly include features extending distally, such as pegs or stems. These extensions penetrate below the surface of the tibial plateau and stabilize the tibial tray component against movement. In cementless tibial implants, the outer surfaces of these extensions are typically porous to allow for bone ingrowth. For example, in the Zimmer Trabecular Metal Monoblock tibial trays, pegs with flat distal surfaces and hexagonal axial surfaces are formed completely of a porous metal. In such trays, bone ingrowth is likely to occur along all surfaces of the pegs, including the distal surfaces.

Femoral components of such knee prosthesis systems are also designed for either cemented or cementless fixation. For cemented fixation, the femoral component typically includes recesses or cement pockets. For cementless fixation, the femoral component is designed for primary fixation through a press-fit, and includes porous bone-engaging surfaces suitable for bone ingrowth. Both designs may include pegs designed to extend into prepared holes in the femur for stabilization of the implant.

On occasion, the primary knee prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary knee prosthesis (or parts of it) is removed and replaced with components of a revision prosthetic system.

When the tibial or femoral implant includes extensions (such as pegs or stems) that extend into the natural bone, a revision surgery usually requires resection of the bone in order to dislodge the extensions from the bone. This resection complicates the surgery and does not dislodge the extensions from the bone, and subsequent removal of the implant with the intact extensions often results in the removal of more of the patient's natural bone than is desirable. This removal of additional bone may further compromise the bone, increase the risk of onset of bone pathologies or abnormalities, or reduce the available healthy bone for fixation of the revision implant. Moreover, the large resection usually means that a larger orthopaedic implant is necessary to fill the space and restore the joint component to its expected geometry.

This difficulty in dislodging the primary implant components from the bones is worsened by the fact that bone also grows into the extensions. Severing these connections may be problematic since not all of these areas are easily accessible without resecting large amounts of bone.

Similar issues may be presented in other types of joint prostheses.

The assignee of the present application has filed patent applications related to the use of porous metal pegs in prostheses. These patent applications include the following: U.S. Pat. Pub. No. 20110029090 A1 entitled "Prosthesis With Modular Extensions"; U.S. Pat. Pub. No. 20110035017 A1 entitled "Prosthesis With Cut-Off Pegs And Surgical Method"; U.S. Pat. Pub. No. 20110035018 A1 entitled "Prosthesis With Composite Component"; U.S. Pat. Pub. No. 20110106268 A1 entitled "Prosthesis For Cemented Fixation And Method For Making The Prosthesis". The disclosures of all of these patent applications are incorporated by reference herein in their entireties.

Use of the extensions disclosed, for example, in U.S. Pat. Pub. No. 20110035017, allows the surgeon to cut along the bone-engaging surface of the implant and through the porous metal extensions extending into the bone from the tibial tray platform. This can be accomplished using a bone saw to easily remove the tibial platform during revision surgery. To remove the extensions from the bone, the surgeon may then cut around the outer perimeter of each extension with a saw such as a trephine saw. Each extension may then be readily removed from the bone.

U.S. Pat. Pub. Nos. 20110106268, 20110035017, 20110029092 and 20110029090 disclose sintering porous metal pegs onto a solid metal base as well as mounting the porous metal pegs on solid metal studs without sintering (through a Morse taper connection, for example). Sintering to form a metallurgical bond can be challenging in practice, particularly if the solid metal base comprises a Co—Cr—Mo alloy and the peg comprises a titanium foam; these metals are not compatible at sintering temperatures and bonding between these metals can result in the formation of brittle intermetallic materials at the interface. These brittle intermetallic materials can have unacceptable mechanical properties. Accordingly, for some materials, a mechanical connection is preferable. And while means of mechanically connecting porous and solid metal parts of an implant component disclosed in U.S. Pat. Pub. Nos. 20110106268, 20110035017, 20110029092 and 20110029090, it is desirable to explore other options for mechanical connecting porous and solid metal parts, options that may be more cost-effective or may result in advantageous properties.

SUMMARY

The present invention addresses the need for a joint prosthesis that is suitable for cementless fixation, that can be removed more readily from the bone in revision surgery to conserve native bone and that is made of porous and solid metal components that are mechanically fixed together. In addition, a method of making such a prosthesis is disclosed. While the illustrated embodiments of the invention address all of these needs, it should be understood that the scope of the invention as defined by the claims may include prostheses that address one or more of these needs. It should also be understood that various aspects of the present invention provide additional advantages, as set forth more fully below. In addition, it should be understood that the principles of the present invention may be applied to knee prostheses as well as other joint prostheses, such as, for example, an ankle prosthesis.

In one aspect, the present invention provides a joint prosthesis comprising a first component having a solid metal portion and a porous metal portion. The solid metal portion includes a first solid metal surface and a second solid metal surface spaced from the first solid metal surface. An internal wall extends from the second solid metal surface toward the first solid metal surface and has an end at a level between the first solid metal surface and the second solid metal surface. The internal wall is tapered to have a minimum internal diameter furthest from the first solid metal surface and a larger internal diameter at the end of the internal wall and to define an internal chamfered chamber. The second solid metal surface has an opening at the junction of the internal wall and the second solid metal surface. The porous metal portion includes a peg having a head and a shaft. The head of the peg has a first free end and a tapered wall extending from the junction of the head and the shaft toward the first free end. The peg has a maximum outer diameter at the first free end and a smaller outer diameter at the junction of the head and the shaft. At least a substantial part of the head of the peg is received within the chamfered chamber in the solid metal portion between the first solid metal surface and the second solid metal surface. A portion of the peg extends outward through the opening in the second solid metal surface. The solid metal portion extends from the first solid metal surface to the head of the peg and covers the head of the peg. There is no metallurgical connection between the peg and the second solid metal surface of the solid metal portion.

In an exemplary embodiment, the solid metal portion and porous metal portion comprise different metals. For example, the solid metal portion may include cobalt (and in particular, an alloy of cobalt, chromium and molybdenum) and the porous metal portion may include titanium (and in particular, a titanium metal foam).

In another exemplary embodiment, the first component comprises a distal femoral implant component having articular surfaces and bone-facing surfaces. In this embodiment, the first surface comprises one of the articular surfaces and the second surface comprises one of the bone-facing surfaces. The joint prosthesis may further comprise a bearing having articular surfaces to receive the articular surfaces of the distal femoral implant component.

The bearing in this embodiment may have a mounting surface spaced from the articular surfaces of the bearing. The prosthesis may further comprise a tibial tray having a support surface to accept the mounting surface of the bearing. In one particular embodiment, the tibial tray and bearing are fixed bearing, and the mounting surface of the bearing and support surface of the tibial tray have complementary structures to fix the bearing to the tibial tray. The complementary structures may include a solid metal anterior buttress extending proximally from and being continuous with the support surface of the tray. In one of the illustrated embodiments, a portion of the anterior buttress overlies at least a portion of the head of the peg and solid metal extends between the anterior buttress and the head of the peg.

In another exemplary embodiment, the solid metal portion includes a solid metal annulus surrounding the peg. The solid metal annulus in this embodiment is continuous with and extends from the second solid metal surface of the solid metal portion of the first component. In this particular embodiment, there is no metallurgical bond between the solid metal annulus and the peg. In this particular embodiment, the metal annulus may extend radially outward about 1 mm out from the surface of the peg. Moreover, in this particular embodiment, the metal annulus may have a tapered inner wall continuous with the tapered inner wall of the chamfered chamber so that the chamfered chamber extends beyond the level of the second solid metal surface to allow for use of a peg having a longer head to maximize contact between the head of the peg and the chamfered chamber.

In any of the embodiments, a layer of porous metal may be metallurgically bonded to the second solid metal surface. In embodiments having a metal annulus, the layer of porous metal may extend to the solid metal annulus.

In any of the embodiments, there may be an annular gap in the solid metal portion adjacent to the first free end of the head of the peg.

In any of the embodiments, the internal wall of the chamfered chamber may define an angle of about 40 degrees with a central longitudinal axis of the chamfered chamber.

In any of the embodiments, the solid metal portion of the tray may have a thickness of less than 5 mm between the first solid metal surface and the second solid metal surface.

In another aspect, the present invention provides a method of making a joint prosthesis from a solid metal base, a porous metal peg and a solid metal plug.

In this aspect of the invention, the solid metal base includes a first solid metal surface and a second solid metal surface spaced from the first solid metal surface. There is a hole in the first solid metal surface, and another hole in the second solid metal surface. An internal wall extends between and defines these holes. The internal wall has a tapered portion and a cylindrical portion. The tapered portion has a minimum internal diameter at the second solid metal surface and a maximum outer diameter at a position between the first solid metal surface and the second solid metal surface. The cylindrical portion of the internal wall extends from the tapered portion to the edge defining the hole in the first solid metal surface. The tapered portion of the internal wall defines a chamfered chamber and the cylindrical portion defines a cylindrical chamber.

In this aspect of the invention, the peg includes a head and a shaft. The head has a first free end, an end surface at the first free end and a tapered wall extending from the first free end to the junction of the head and the shaft. The maximum outer diameter of the peg is at the first free end and a smaller outer diameter of the peg is at the junction of the head and the shaft.

In this aspect of the invention, the plug includes a first solid metal surface, a second solid metal surface and a side wall extending from the first solid metal surface toward the second solid metal surface.

In this aspect of the invention, the method includes positioning the peg with the tapered wall of the head bearing against the tapered portion of the internal wall and with the shaft of the peg exposed past the second solid metal surface of the solid metal base. The end surface of the head of the peg does not extend beyond the junction of the chamfered chamber and the cylindrical chamber in the solid metal base. The plug is press-fit into the cylindrical chamber in the solid metal base with the second solid metal surface of the plug bearing against the end surface of the head of the peg and with the side wall of the plug engaging the cylindrical portion of the internal wall defining the cylindrical chamber. The solid metal plug is then fixed to the first solid metal surface of the solid metal base. Undesirable portions of the solid metal plug that extend beyond the first solid metal surface of the base are then removed.

In an exemplary embodiment, the cylindrical chamber of the solid metal base has an internal diameter. The first solid metal surface of the plug has an outer diameter. The first solid metal surface of the plug and the side wall of the plug define a first cylindrical portion. The second solid metal surface of the plug has a different outer diameter. The second solid metal surface of the plug and the side wall of the plug define a second cylindrical portion. The outer diameter of the first cylindrical portion of the plug is greater than the outer diameter of the second cylindrical portion of the plug. The inner diameter of the cylindrical chamber and the outer diameter of the first cylindrical portion of the plug are dimensioned to allow for the first cylindrical portion of the plug to be press-fit into the cylindrical chamber.

In a more particular embodiment, there is no contact between the second cylindrical portion of the plug and the internal wall of the solid metal base after the first cylindrical portion of the plug has been press-fit into the cylindrical chamber.

In another more particular embodiment, the first cylindrical portion of the plug has an axial length and the cylindrical chamber of the solid metal base has an axial length. The axial length of the first cylindrical portion of the plug is greater than the axial length of the cylindrical chamber of the solid metal base.

In another more particular embodiment (fixed bearing), the solid metal base includes an anterior buttress extending outward from the first solid metal surface to a height. In this embodiment, the axial length of the first cylindrical portion of the plug is great enough to extend to the height of the anterior buttress so that a portion of the first cylindrical portion of the plug is exposed above the first solid metal surface of the solid metal base. In this embodiment, the method includes fixing the first cylindrical portion of the plug to the anterior buttress and removing a portion of the first cylindrical portion of the plug after fixing so that a portion of the first cylindrical portion of the plug defines a portion of the anterior buttress.

In another exemplary embodiment, the second solid metal surface of the solid metal base includes a solid metal annulus surrounding the hole in the second solid metal surface. The annulus extends outward from the second solid metal surface to an outer surface.

In a more particular embodiment, the axial distance from a plane at the outer surface of the annulus to a plane through the junction of the cylindrical chamber and chamfered chamber is substantially the same as the axial length of the head of the peg.

In a more particular embodiment, the outer diameter of the annulus is no more than 2 mm greater than the inner diameter of the annulus.

In a more particular embodiment, the method further comprises the step of coating the second solid metal surface of the solid metal base with porous metal around the annulus and sintering the porous metal coating to the solid metal base.

In a more particular embodiment, the outer surface of the annulus and the exposed surface of the porous metal coating are substantially co-planar.

In another exemplary embodiment, the step of press-fitting the plug into the cylindrical chamber compresses the head of the peg.

In another exemplary embodiment, the peg comprises a metal foam containing titanium, the solid metal base comprises an alloy containing cobalt and the solid metal plug comprises an alloy containing cobalt.

In another exemplary embodiment, the solid metal base includes a plurality of cylindrical chambers and a plurality of chamfered chambers. A plurality of porous metal pegs are provided, and one porous metal peg is positioned within each chamfered chamber. A plurality of solid metal plugs are provided, and one solid metal plug is press-fit into each cylindrical chamber. Each solid metal plug is fixed to the solid metal base and any undesirable excess of any plug extending beyond the first solid metal surface of the base is removed.

In another exemplary embodiment, the joint prosthesis comprises a prosthetic knee implant having a proximal tibial implant component, a distal femoral implant component and a bearing.

In another exemplary embodiment, the solid metal base is part of the proximal tibial component and the first solid metal surface defines a support surface for the bearing. In this embodiment, the method may further comprise the step of polishing the first solid metal surface after the step of removing any undesirable portion of the solid metal plug extending beyond the first solid metal surface of the base.

In any of the above embodiments, the step of fixing may comprise welding, and in more particular, may comprise laser welding.

In another aspect, the present invention provides an orthopaedic prosthesis comprising a first component having a solid portion and a porous portion. The solid portion includes a first solid surface and a second solid surface spaced from the first solid surface. An internal wall extends from the second solid surface toward the first solid surface and has an end at a level between the first solid surface and the second solid surface; this internal wall defines a chamber. The second solid surface has an opening at the junction of the internal wall and the second solid surface. The porous portion includes a peg having a head and a shaft. At least a substantial part of the head of the peg being is within the chamber in the solid portion between the first solid surface and the second solid surface. A portion of the peg extends outward through the opening in the second solid surface. The solid portion of the component extends from the first solid surface to the head of the peg and covers the head of the peg. The peg and the second solid surface of the solid portion are not bonded together.

In a more particular embodiment, the solid portion of the first component comprises metal.

In another more particular embodiment, the peg comprises porous metal.

In another more particular embodiment, the chamber in the solid portion is frusto-conical in shape.

In another more particular embodiment, the head of the peg is frusto-conical in shape.

In another aspect, the present invention provides a method of making a joint prosthesis from a solid base, a porous peg and a solid plug. The solid base includes a first solid surface and a second solid surface spaced from the first solid surface, a hole in the first solid surface, a hole in the second solid surface and an internal wall extending between and the holes and defining a chamber. The peg includes a head and a shaft. The head has a first free end, and the peg has a maximum outer diameter at the first free end and a smaller outer diameter at the junction of the head and the shaft. The plug includes a first solid surface, a second solid surface spaced from the first solid surface and a side wall extending from the first solid surface toward the second solid surface. The method comprises positioning the peg in the chamber in the solid base. The plug is press-fit into the chamber in the solid base with the second solid surface of the plug bearing against the end surface of the head of the peg. The solid plug is fixed to the first solid surface of the solid base. Any undesirable portion of the solid plug extending beyond the first solid surface of the base is then removed.

In a more particular embodiment, the solid base and the plug of the first component comprise metal.

In another more particular embodiment, the peg comprises porous metal.

In another more particular embodiment, the chamber and the head of the peg are frusto-conical in shape.

In another more particular embodiment, the step of fixing the solid plug to the first solid surface of the solid base comprises welding.

BRIEF DESCRIPTION OF THE DRAWINGS

The detailed description particularly refers to the following figures, in which.

DETAILED DESCRIPTION

Figure 1:
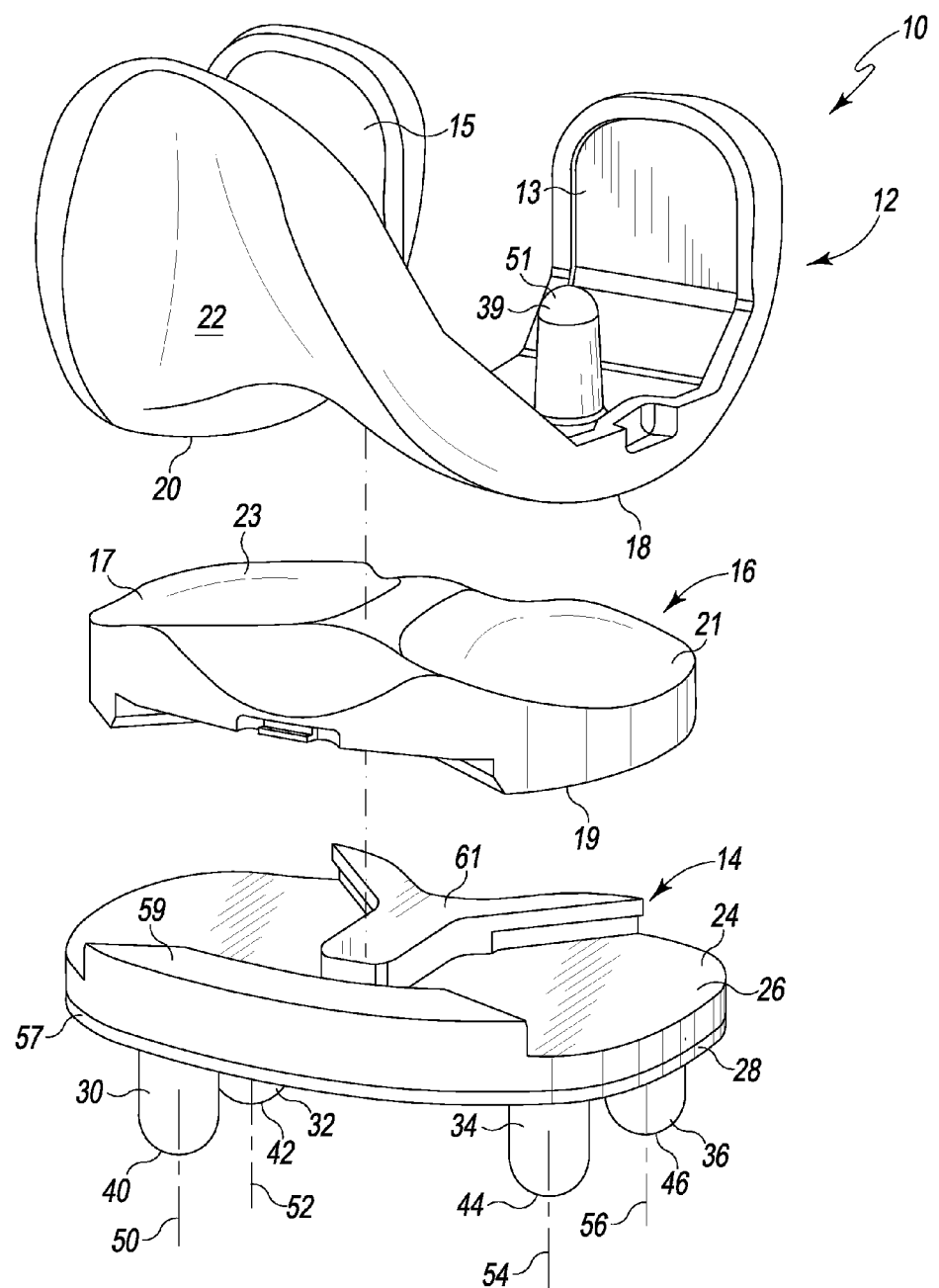
FIG. 1 is an exploded perspective view of a fixed-bearing knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, there is shown a knee prosthesis 10. The knee prosthesis 10 includes a femoral component 12, a tibial tray 14, and a bearing 16. The illustrated knee prosthesis 10 is a fixed bearing knee prosthesis, meaning that no movement is intended to occur between the tibial tray 14 and the bearing 16. It should be understood that the principles of the present invention may also be applied to mobile bearing designs, such as rotating platform tibial trays, as well as to other joint prostheses.

The illustrated femoral component 12 includes two condylar articulation surfaces: a medial condyle articulation surface 18 and a lateral condyle articulation surface 20. These articulation surfaces 18, 20 are solid metal. The femoral component 12 is configured to be implanted into a surgically prepared end of the patient's femur (not shown), and is configured to generally emulate the configuration of the patient's natural femoral condyles. As such, the lateral condyle surface 20 and the medial condyle surface 18 are configured (e.g., curved) in a manner which generally mimics the condyles of the natural femur.

The specific curvatures of the condyles in the sagittal plane (the "J-curve") and coronal plane may be like those in standard, commercially available implants, such as those available from DePuy Synthes Sales, Inc., as well as those available from other suppliers of prosthetic knee systems. The femoral component 12 may also incorporate the J-curves and may also include other features described in the following United States patent applications, the disclosures of which are incorporated by reference herein in their entireties: "Orthopaedic Knee Prosthesis Having Controlled Condylar Curvature," U.S. Pat. No. 8,236,061; "Posterior Cruciate-Retaining Orthopaedic Knee Prosthesis Having Controlled Condylar Curvature," U.S. Pat. No. 8,192,498; "Orthopaedic Femoral Component Having Controlled Condylar Curvature," Ser. No. 12/165,579; Ser. No. 12/165,582; and "Posterior Stabilized Orthopaedic Knee Prosthesis Having Controlled Condylar Curvature," U.S. Pat. No. 8,187,335.

Referring again to FIG. 1, the lateral condyle surface 20 and the medial condyle surface 18 are spaced apart from one another thereby defining an intercondylar articulation surface 22 therebetween. The intercondylar articulation surface 22 defines a patella groove shaped to receive and bear against a patella implant component (not shown). The intercondylar articulation surface 22 may comprise solid metal.

The femoral component 12 also includes bone-facing surfaces 13, 15 opposite the articulation surfaces 18, 22. Some or all of the bone-facing surfaces 13, 15 may comprise solid metal (as described below) conducive to bony ingrowth. Alternatively, the bone-facing surfaces of the femoral component may include cement pockets to facilitate cementing the component to the bone.

The femoral component 12 of FIG. 1 is a cruciate retaining component, although it should be understood that the principles of the present invention are applicable to cruciate substituting prosthetic knee systems as well.

The articulation surfaces of the femoral component 12 may be constructed from a biocompatible metal, such as stainless steel, titanium, cobalt chrome molybdenum alloy or titanium alloy, although other materials may also be used. Commonly used alloys include titanium alloy Ti-6Al-4V. Any biocompatible metal having characteristics suitable for the intended use may be used for the solid metal portions of the femoral component 12.

Instead of metal, a polymer material such as polyetheretherketone (PEEK) could be used for the femoral component 12.

As shown in FIG. 1, the bearing component 16 has a proximal articulation surface 17 and a distal mounting surface 19 opposite the proximal articulation surface 17. The proximal articulation surface 17 of the bearing 16 includes a medial bearing surface 21 configured to articulate with the medial condyle 18 of the femoral component 12 and a lateral bearing surface 23 configured to articulate with the lateral condyle 20 of the femoral component 12. The bearing component 16 is modular, and is assembled with the tibial tray 14 intraoperatively and secured thereto through a mechanical interlocking mechanism, as described in more detail below.

The bearing 16 may be made of a polymeric material. Suitable polymeric materials for the bearing 16 include ultra-high molecular weight polyethylene (UHMWPE). The UHMWPE may comprise a cross-linked material, for example. Techniques for crosslinking, quenching, or otherwise preparing UHMWPE are described in numerous issued U.S. patents, examples of which include: U.S. Pat. No. 5,728,748 (and its counterparts) issued to Sun, et al.; U.S. Pat. No. 5,879,400 issued to Merrill et al.; U.S. Pat. No. 6,017,975 issued to Saum, et al.; U.S. Pat. No. 6,242,507 issued to Saum et al.; U.S. Pat. No. 6,316,158 issued to Saum et al.; U.S. Pat. No. 6,228,900 issued to Shen et al.; U.S. Pat. No. 6,245,276 issued to McNulty et al.; and U.S. Pat. No. 6,281,264 issued to Salovey et al. The disclosure of each of these U.S. patents is incorporated by reference herein in their entireties. The UHMWPE of the bearing material may be treated to stabilize any free radicals present therein, such as through the addition of an antioxidant such as vitamin E. Techniques for stabilizing UHMWPE with antioxidants are disclosed, for example, in U.S. Pat. Pub. No. 20070293647A1 (Ser. No. 11/805,867) and U.S. Pat. Pub. No. 20030212161A1 (Ser. No. 10/258, 762), both entitled "Oxidation-Resistant And Wear-Resistant Polyethylenes For Human Joint Replacements And Methods For Making Them," the disclosures of which are incorporated herein in their entireties. It should be understood that the present invention is not limited to any particular UHMWPE material or to UHMWPE material for the bearing 16 unless expressly called for in the claims. It is expected that other materials for the bearing 16 are or will become available that will be useful in applying the principles of the present invention.

The tibial tray 14 includes a solid metal base 24 having a solid metal proximal mounting surface 26 and an opposite second surface 28. The illustrated tibial tray 14 also includes a plurality of porous metal pegs 30, 32, 34, 36, extending distally from the second surface 28 of the solid metal base to distal ends 40, 42, 44, 46, along longitudinal axes 50, 52, 54, 56, intersecting the distal surface 28 of the platform 24. Although the tibial tray 14 of the illustrated embodiment does not include a distally extending stem, it should be understood that such tibial trays are within the scope of the present invention unless expressly excluded by the claims.

In the illustrated embodiment, the tibial tray 14 is intended for use without bone cement. A porous metal coating 57 is on the second surface 28 of the solid metal base 24 to facilitate bone ingrowth for fixation.

The femoral component 12 may also include porous metal pegs and a porous metal coating on the bone-facing surfaces 13, 15. For example, porous metal pegs may extend proximally from the bone-facing surfaces 13, 15 of the femoral component 12. One such peg is illustrated in FIG. 1 at 39. This peg also has a proximal end 51, a thickness, and a length.

In the illustrated femoral component and tibial tray, each peg 30, 32, 34, 36, 39 extends outward from a junction with the bone-facing surfaces 13, 15, 28 of their respective implant components 12, 14 to their opposite ends 40, 42, 44, 46, 51. The pegs 30, 32, 34, 36, 39 have exposed outer surfaces past the junctions. The pegs 30, 32, 34, 36 are configured to be implanted into a surgically prepared end of a patient's tibia or femur (not shown) and are configured for stabilizing the tibial component 14 and femoral component 12, when implanted in the bones of a patient. Bone may grow into the exposed outer surfaces of the pegs for fixation of the implant components on the tibia and femur.

Figure 3:
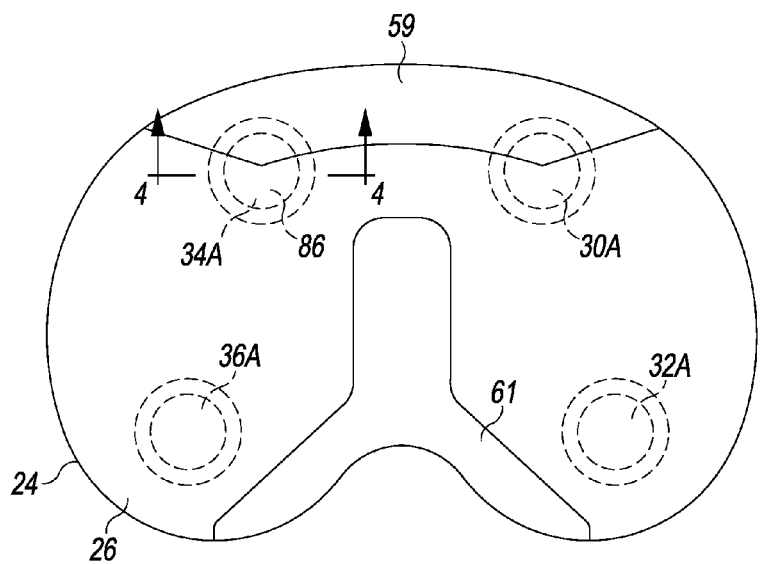
FIG. 3 is a top plan view of the tibial tray of the knee prosthesis of FIG. 1.

The end surfaces of the pegs could be flat, spheroidal or some other shape. In the embodiment of FIG. 1, the distal ends 40, 42, 44, 46, 51 are generally spheroidal. The exemplary peg illustrated in FIGS. 3-5, 8-10, 15 and 17 has a flat distal end. This exemplary peg is identified with reference number 34A (its distal end as 44A and its longitudinal axis as 54A) in FIGS. 3-4, 8-10, 14-15 and 17 (the remaining pegs in FIGS. 3 and 14 being identified as 30A, 32A and 36A). It should be understood that the description applies to all of the illustrated pegs 30, 30A, 32, 32A, 34, 34A, 36, 36A, the only difference in the illustrated pegs being the shape of the distal surfaces.

Referring again to FIG. 1, the configuration of the proximal mounting surface 26 of the solid metal base 24 of the tibial tray 14 may vary depending on the type of implant. For example, if the prosthesis is a rotating platform type of mobile bearing knee prosthesis, the proximal mounting surface 26 of the tibial tray 14 and the distal mounting surface 19 of the bearing 16 will be smooth to allow for rotation of the bearing on the mounting surface 26 of the tibial tray 14, 14A. The illustrated embodiment is a fixed bearing design; the proximal mounting surface 26 of the tibial tray 14 and the distal mounting surface 19 of the bearing 16 in this illustration include complementary locking features that eliminate or at least minimize any relative movement between the bearing 16 and the tibial tray 14 when these components are assembled. These complementary locking features in the illustrated embodiment include pedestals and recesses (not shown) on the distal surface 19 of the bearing 16 and buttresses 59, 61 and undercuts on the proximal mounting surface 26 of the solid metal base 24 of the tibial tray 14. Detailed descriptions of this and other designs for fixed bearing tibial trays may be found, for example, in the following U.S. patent and patent application, the disclosures of which are incorporated by reference herein in their entireties: U.S. Pat. No. 7,628,818, entitled "Fixed-Bearing Knee Prosthesis Having Interchangeable Components", filed on Sep. 28, 2007; U.S. patent application Ser. No. 11/860,833, entitled "Fixed-Bearing Knee Prosthesis", filed on Sep. 25, 2007 and published as US 20090082873 A1. It should be understood that the illustrated complementary locking features are provided as an example; the invention is not limited to fixed bearing prostheses or to any particular locking mechanism for fixed bearing prostheses unless expressly called for in the claims.

Figure 4:
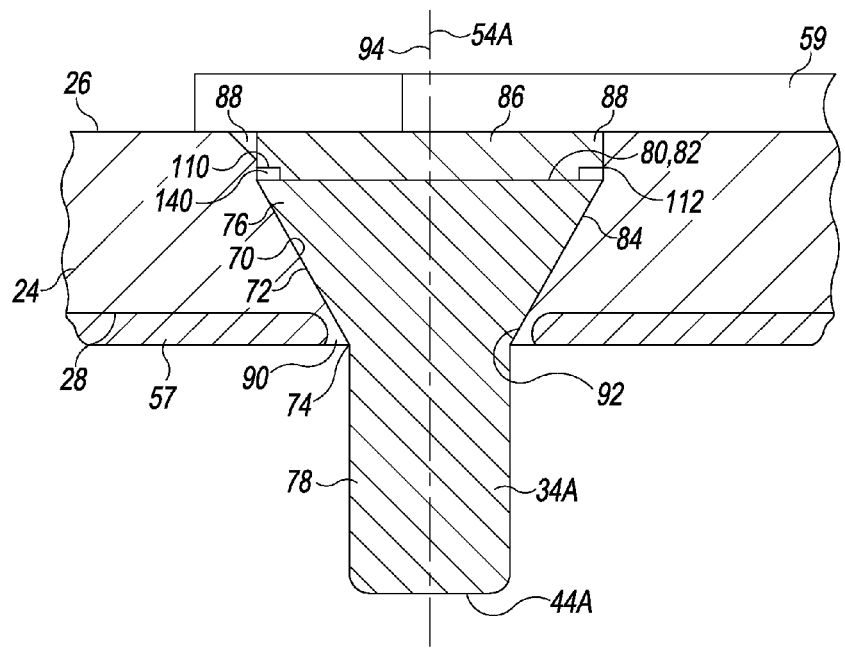
FIG. 4 is a partial cross-sectional of the tibial tray of FIG. 3, taken along line 4-4 of FIG. 3, as viewed in the direction of the arrows.

FIG. 4 illustrates, in cross-section, the mechanical locking mechanism for fixing the porous metal peg 34A to the solid metal tibial base 24. It should be understood that the same mechanical connection can be used for locking all of the porous metal pegs to the solid metal base, including previously described porous metal pegs 30, 30A, 32, 32A, 34, 36 and 36A. As shown in FIG. 4, the solid metal base 24 includes an internal wall 70 that extends from the second surface 28 of the base 24 toward the mounting surface 26. The illustrated internal wall 70 is tapered to have a distal minimum inner diameter furthest from the mounting surface 26 and a larger inner diameter nearer to the mounting surface 26. The internal wall 70 defines an internal chamfered chamber 72. The second solid metal surface 28 of the base 24 has a circular opening 74 at the distal end of the internal wall 70.

The peg 34A has a head 76 and a shaft 78. The head 76 of the peg 34A has a free end 80 defining a flat surface 82 and a tapered surface 84 extending from the first free end 80 to the junction of the head 76 and the shaft 78. The maximum outer diameter of the peg 34A is at the first free end 80 and a smaller outer diameter at the junction of the head 76 and the shaft 78.

As shown in FIG. 4, at least a substantial part of the head 76 of the peg 34A is received within the chamfered chamber 72 in the solid metal base 24 between the surfaces 26, 28 of the base 24. A portion of the shaft 78 of the peg 34A extends outward through the circular opening 74 to its distal end 44A. As illustrated, a length of the porous metal shaft is exposed beyond the surface 28 and porous metal coating 57.

As illustrated in FIG. 4, solid metal 86 covers and bears against the head 76 of the peg 34A. This solid metal 86 is connected to the remainder of the solid metal mounting surface 26 by a circular weld 88 in the illustrated embodiment. In the finished product, the solid metal mounting surface 26 appears to be continuous: there is no discernible difference between the metal 86 covering the head and the remainder of the mounting surface 26. The solid metal 86 holds or compresses the tapered surface 84 of the head 76 of the peg 34A against the tapered internal wall 70 of the chamfered chamber 72 to mechanically fix the porous metal peg 34A to the solid metal base 24. There is no metallurgical connection between the peg 34A and the base 24; that is, the porous metal peg 34A is not sintered or welded to the solid metal base 24.

Since there is no need for a metallurgical connection to fix the pegs 30, 30A, 32, 32A, 34, 34A, 36, 36A to the solid metal base 24, different materials may be used for the solid metal portions and the porous metal pegs. For example, the solid metal base 24 may comprise a CoCrMo (cobalt chromium molybdenum) alloy and the porous metal pegs 30, 30A, 32, 32A, 34, 34A, 36, 36A may comprise porous titanium and still be rigidly fixed together. Alternatively, both the solid metal base 24 and the pegs 30, 30A, 32, 32A, 34, 34A, 36, 36A may comprise the same or different forms of titanium, for example. It should be understood that particular metals are indentified as examples only; the present invention is not limited to any particular metal unless expressly called for in the claims. Moreover, it may be desirable to make the base out of a polymer material such as solid PEEK (polyetheretherketone), provided the polymer material posseses adequate mechanical properties. More particularly, fiber-reinforced PEEK, such as PEEK reinforced with carbon fibers or glass fibers may have adequate mechanical properties (strength and stiffness) for this application.

Still referring to FIG. 4, on the distal side, the shaft 78 of the peg 34A and the circular opening 74 in the surface 28 are surrounded by a narrow solid metal annulus 90. The solid metal annulus 90 is co-extensive with and part of the remainder of the base 24, and extends distally from the plane of the majority of the surface 28. As shown in FIG. 4, annulus 90 has a tapered internal wall 92 continuous with the tapered internal wall 70 so that the chamfered chamber 72 extends beyond the plane of the majority of the surface 28 to the distal end of the annulus 90. The tapered internal walls 70 and 92 define an angle of about 40 degrees with the central longitudinal axis 94 of the chamfered chamber 72 in the illustrated embodiment. It should be understood that this angle is provided as an example only. This angle could be optimized through engineering analysis, such as finite element analysis, and through testing (such as static and dynamic pull-out and shear testing of the peg). The invention is not limited to any particular angle unless expressly called for in the claims.

In a typical tibial tray, the thickness of the tray between the surfaces 24 and 26 is on the order of 5 mm or less. Including the annulus 90 in the design effectively extends the length of the chamfered chamber 72 and allows for use of a peg with a longer (axially) head to optimize the mechanical lock between the components 24, 34A in the limited space available.

In a medial-lateral direction, the annulus 90 is narrow: the difference between the inner diameter and outer diameter is on the order of 2 mm so that the outer diameter of the annulus 90 is on the order of 2 mm larger than the outer diameter of the shaft 78 of the peg 34A. The porous metal coating 57 on the surface 28 extends up to the outer edge of the annulus 90 to maximize the area of porous metal exposed for bone ingrowth in the vicinity of the pegs. It should be understood that the dimensions for the annulus 90 and illustrated shape of the annulus 90 are provided as examples only; the invention is not limited to any particular shape or dimension unless expressly called for in the claims. Moreover, although the illustrated annulus increases the engagement between the head of the peg and the internal wall of the base 24, the invention is not limited to use of such an annulus unless expressly called for in the claims.

Figure 2:
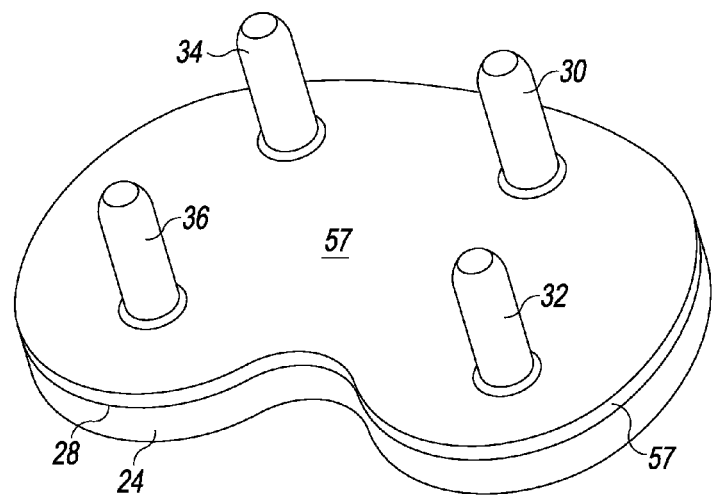
FIG. 2 is a bottom perspective view of the tibial tray of the knee prosthesis of FIG. 1.
Figure 5:
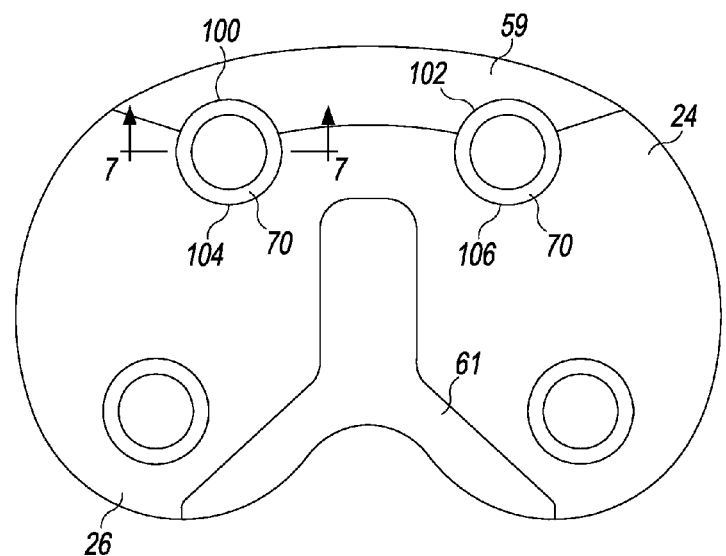
FIG. 5 is a top plan view of a tibial base used in making the tibial tray of FIGS. 1-4.
Figure 6:
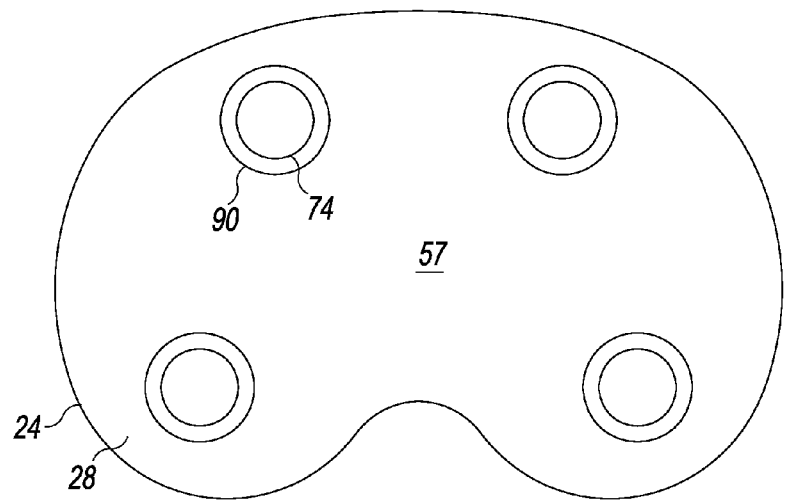
FIG. 6 is a bottom plan view of the tibial base of FIG. 5.
Figure 7:
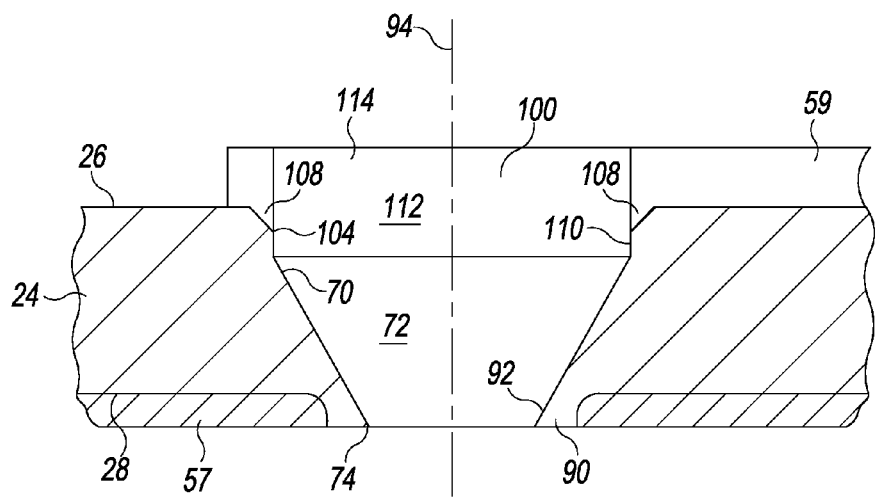
FIG. 7 is a partial cross sectional view of the tibial base of FIGS. 5-6 taken along the line 7-7 of FIG. 5, as viewed in the direction of the arrows.

Turning to FIGS. 5-7, the solid metal base 24 is illustrated as it would appear early in the manufacturing process, before the pegs are mounted to the base. As shown in FIG. 5, the anterior buttress 59 includes a pair of cutouts 100, 102 surrounding circular openings 104, 106 in the mounting surface 26. As shown in FIG. 7, a small annular depression 108 may be provided around each circular opening 104 for use in welding components together later in the manufacturing process. The cutouts 100, 102 in the anterior buttress are provided to accommodate the anterior pegs and plugs that will be used later in the manufacturing process. The cutouts 100, 102 are only necessary in the illustrated embodiment because, as shown in FIG. 2, two pegs 30A, 34A underlie a portion of the anterior buttress 59 in the final tibial tray illustrated in FIGS. 1-3.

As shown in FIG. 7, an internal wall 110 extends from the proximal end of the tapered internal wall 70 to the mounting surface 26. The internal wall 110 is cylindrical in shape between the mounting surface 26 and the chamfered chamber 72 and defines a cylindrical chamber 112. Above the mounting surface 26, an external wall 114 extends from the internal wall 110 and defines a surface of the cutout 100 in the anterior buttress 59. The internal walls 70, 110 and external wall 114 are continuous, and may be considered to comprise different portions of a single wall. The inner diameter of the cylindrical chamber 112 is large enough for the head 76 of the peg to fit through.

As discussed above, the surface 28 opposite the mounting surface 26 of the solid metal base 24 has a porous metal coating 57 in the illustrated embodiment. One type of porous coating which may be used as the porous portion 57 of the base 24 is Porocoat® porous coating which is commercially available from DePuy Orthopaedics of Warsaw, Ind. Other examples of porous coatings are disclosed in U.S. Pat. No. 8,066,770, which is incorporated by reference herein in its entirety; the coating described in that patent may be used for the coating 57. It should be understood that these porous coatings are provided as examples only; the invention is not limited to any particular porous coating unless expressly called for in the claims.

Figure 8:
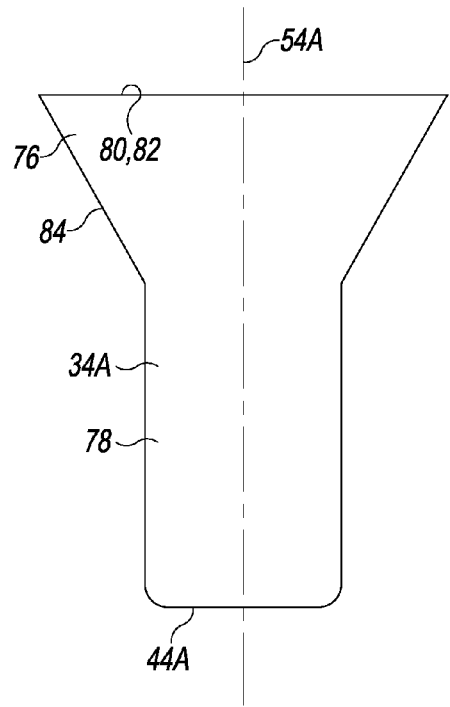
FIG. 8 is a side view of a porous metal peg used in making the tibial tray of FIGS. 1-4.
Figure 9:
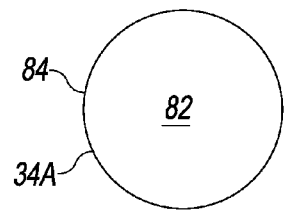
FIG. 9 is a top plan view of the porous metal peg of FIG. 8.
Figure 10:
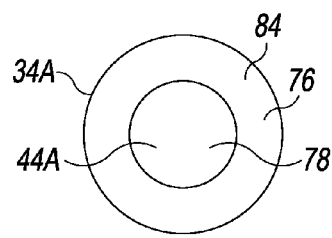
FIG. 10 is a bottom plan view of the porous metal peg of FIGS. 8-9.

Turning to FIGS. 8-10, an example of a porous metal peg 34A is illustrated as it would appear early in the manufacturing process, before being mounted to the solid metal base 24. The structural features of the peg 34A are described above. The illustrated pegs 30, 30A, 32, 32A, 34, 34A, 36, 36A comprise titanium metal foam. Such a foam may be made as taught in the following U.S. patent applications: U.S. Publication No. 20080199720A1 (U.S. patent application Ser. No. 11/677,140), filed on Feb. 21, 2007 and entitled "Porous Metal Foam Structures And Methods"; U.S. Publication No. US 20100098574A1 (U.S. patent application Ser. No. 12/540,617) entitled "Mixtures For Forming Porous Constructs"; U.S. Publication No. 20090326674 A1 (U.S. patent application Ser. No. 12/487,698) entitled "Open Celled Metal Implants with Roughened Surfaces and Method for Roughening Open Celled Metal Implants;" and U.S. Publication No. 20090292365A1 (U.S. patent application Ser. No. 12/470,397) entitled "Implants with Roughened Surfaces"; the disclosures of all of the above patent applications are incorporated by reference herein in their entireties.

The porous metal pegs may have, for example, a bulk porosity (or percent open area or void space) of from about 60% to about 85% (preferably about 60% to about 75%) as measured by volume, the forced intrusion of liquid mercury, and cross-section image analysis. This porosity/void space corresponds with a density of 15-35% (preferably 25-40%) of theoretical density for a similarly sized and shaped solid metal component. The resultant metal foam may be treated to increase its roughness, such as by etching, blasting or by adding irregular powders. The distal ends of the pegs and peripheral surfaces of the porous coating 57 may be smoothed as disclosed in U.S. Pat. Pub. No. 20110029092 A1 to limit bony ingrowth in selected areas or to limit possible abrasion of soft tissue adjacent the edges of surface 57.

Although titanium foam is the preferred material for the pegs, some of the advantages of the present invention may be achieved with alternative materials as well. One example of a suitable alternative material is tantalum porous metal, disclosed, for example in U.S. Pat. No. 5,282,861, entitled "Open Cell Tantalum Structures for Cancellous Bone Implants and Cell and Tissue Receptors," the disclosure of which is hereby incorporated by reference herein. It should be understood that these materials are identified as examples only; the porous metal pegs of the invention are not limited to any particular material, surface finish, porosity or manufacturing process unless expressly called for in the claims.

It may be desirable to use porous pegs having a porosity gradient. For example, it may be desirable for the head 76 to be more dense than the shaft 78. If one were to chose to form a metallurgical bond between the peg 34A and the base 24, it may be more effectively accomplished with a more dense head 76. Alternatively, it may be desirable to smear the surfaces of the head 76 through machining, milling, polishing or smoothing, as disclosed in U.S. Pat. Pub. No. 20110029092 A1.

A variety of techniques are known for treating porous metal implants and may be applied to the pegs and coating of the present invention. For example, calcium phosphate coatings (such as hydroxyapatite) may be applied to the porous portions of the embodiments of the present invention, with or without additional therapeutic agents, as disclosed in U.S. Pat. Pub. No. 20060257358 entitled "Suspension Of Calcium Phosphate Particulates For Local Delivery Of Therapeutic Agents." Alternatively, electrophoretic deposition of a material such as calcium phosphate may be used.

Porous biocompatible polymers are available as well and may possess adequate mechanical properties for use with the present invention, including the pegs 30, 30A, 32, 32A, 34, 34A, 36, 36A of the illustrated tibial tray 14 instead of porous metal. Accordingly, it should be understood that the present invention is not limited to porous metal pegs unless expressly called for in the claims.

Figure 12:
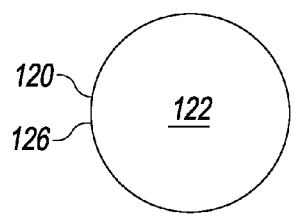
FIG. 12 is a top plan view of the solid metal plug of FIG. 11.
Figure 11:
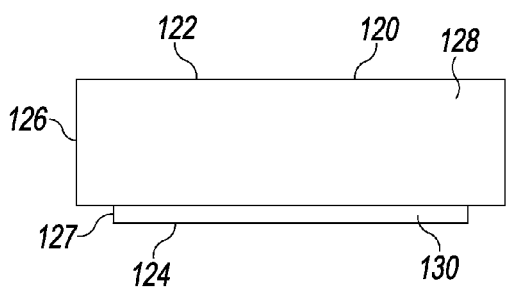
FIG. 11 is a side view of a solid metal plug used in making the tibial tray of FIGS. 1-4.
Figure 13:
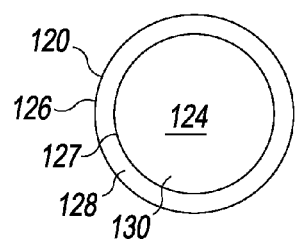
FIG. 13 is a bottom plan view of the solid metal plug of FIGS. 11-12.

Turning to FIGS. 11-13, an example of a plug 120 is illustrated as it would appear early in the manufacturing process, before being mounted to the solid metal base 24. The illustrated plug 120 includes a first solid metal surface 122, a second solid metal surface 124 spaced from the first solid metal surface and a side wall 126 extending from the first solid metal surface 122 toward the second solid metal surface 124. The first solid metal surface 122 of the plug 120 has an outer diameter, and the first solid metal surface 122 of the plug and the side wall 126 of the plug define a first cylindrical portion 128 of the plug. The second solid metal surface 124 of the plug 120 has an outer diameter, and the second solid metal surface 124 of the plug and the reduced diameter side wall 127 of the plug define a second cylindrical portion 130 of the plug. The outer diameter of the first cylindrical portion 128 of the plug is greater than the outer diameter of the second cylindrical portion 130 of the plug. The inner diameter of the cylindrical chamber 112 and the outer diameter of the first cylindrical portion 128 of the plug are dimensioned to allow for the first cylindrical portion 128 of the plug to be press-fit into the cylindrical chamber 112 of the solid metal base 24.

Figure 17:
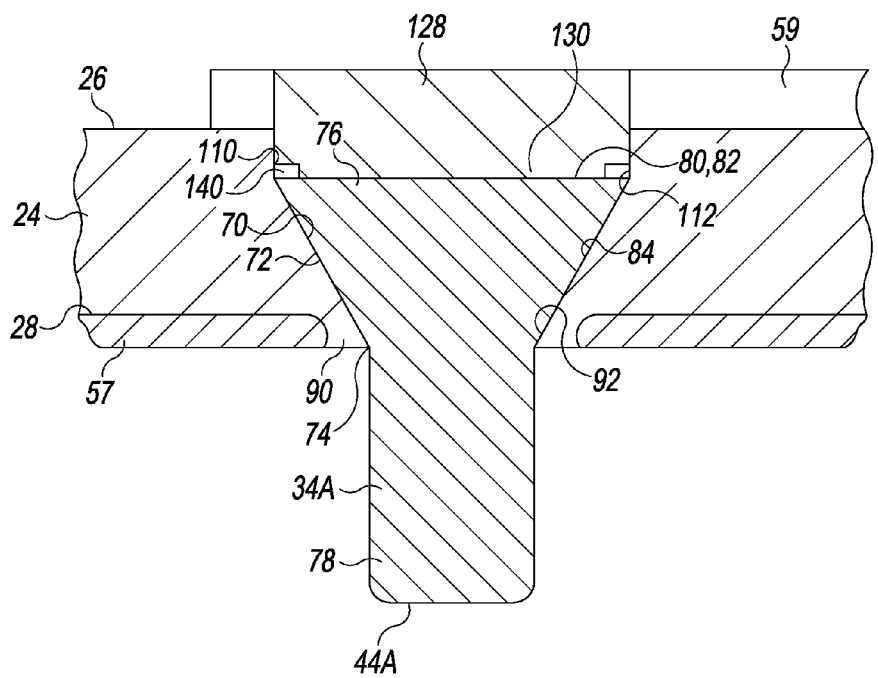
FIG. 17 is a partial cross-sectional view similar to FIGS. 4, 7 and 15, showing a portion of the tibial base, one porous metal peg and one solid metal plug at the intermediate stage of making the tibial tray of FIGS. 1-4 (at the stage illustrated in FIG. 16).

The axial length of the plug 120 between the surfaces 122, 124 is great enough so that when assembled with the peg 34A and the solid metal base 24, the bottom surface 124 of the plug bears against the top surface 82 of the peg 34A and the top surface 122 of the plug 120 is at least level with the top surface of the anterior buttress 59. This assembly is illustrated in FIG. 17. Although the first cylindrical portion 128 of the plug is press-fit in the cylindrical chamber 112 of the base 24, there is no contact between the second cylindrical portion 130 of the plug 120 and the internal wall 70, 110 of the solid metal base 24. An annular gap 140 remains adjacent to and above the top surface 82 of the peg 34A in the first embodiment. This annular gap 140 remains in the final component, as illustrated in FIG. 4.

Figure 16:
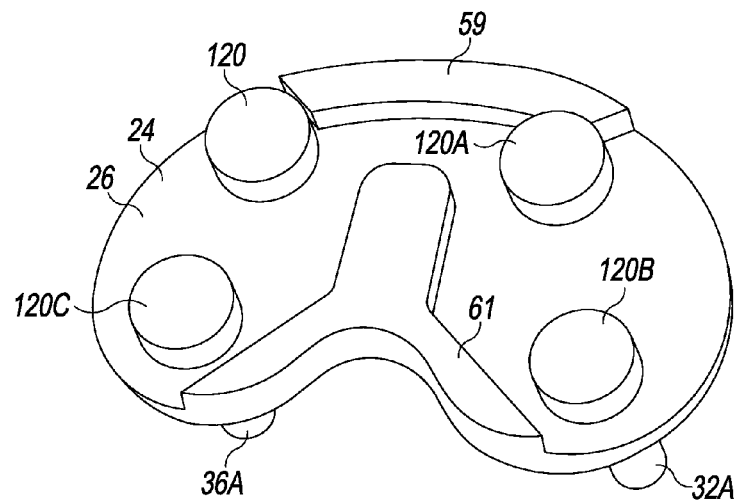
FIG. 16 is a perspective view of the tibial base of FIGS. 5-7, shown with solid metal plugs of the type shown in FIGS. 11-13 at an intermediate stage of making the tibial tray of FIGS. 1-4 (after the stage illustrated in FIGS. 14 and 15)

Since the second cylindrical portion 130 of the plug does not contact the internal walls 70, 110, nothing prohibits the second cylindrical portion 130 from fully engaging the head 76 of the peg 34A to ensure the tapered surface 84 of the peg 34A is fully seated against the tapered internal wall 70. On the proximal side, as shown in FIG. 16, parts of the first cylindrical portions 128 of the anterior plugs 120 fit into and fill the cutouts 100, 102 in the anterior buttress 59.

The annular gap 140 corresponds with the reduced diameter of the second cylindrical portion 130 of the plug and is a vestige of the use of the second cylindrical portion 130 of the first illustrated plug 120 to avoid the plug bottoming out at the transition between the cylindrical chamber 112 and chambered chamber 72. Dimensions of the plug 130 and chambers 72, 112 may be optimized to limit the size of the gap 140 while ensuring that the plug does not bottom out.

The illustrated plugs 120 are solid metal, preferably the same metal used to make the solid metal base 24. For example, if the solid metal base 24 comprises a CoCrMo (cobalt chromium molybdenum) alloy then the plugs would preferably be made of the same CoCrMo alloy. Alternatively, the plugs 120 base may comprise PEEK or fiber-reinforced PEEK, as described above for the base.

Figure 14:
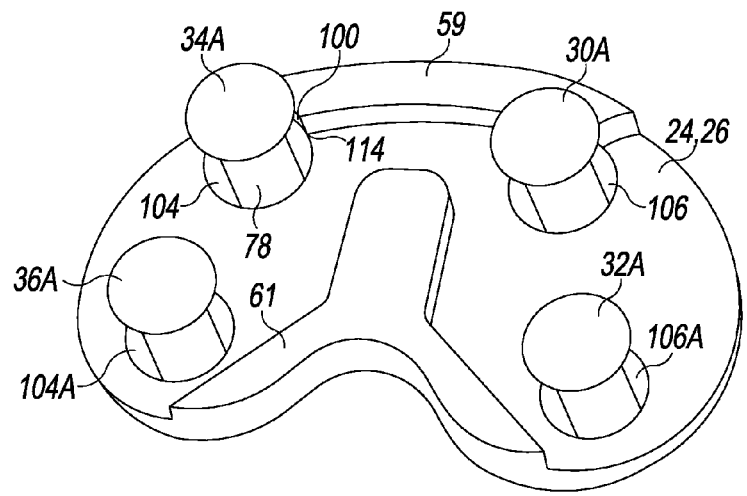
FIG. 14 is a perspective view of the tibial base of FIGS. 5-7, shown with porous metal pegs of the type shown in FIGS. 8-10 at an intermediate stage of making the tibial tray of FIGS. 1-4.
Figure 15:
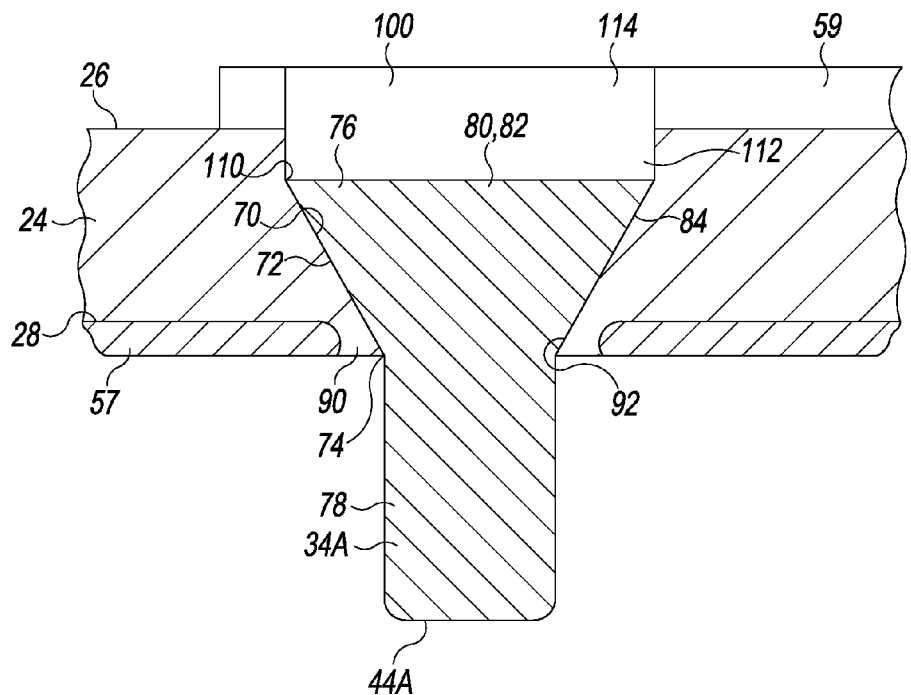
FIG. 15 is a partial cross-sectional view similar to FIGS. 4 and 7, showing a portion of the tibial base and one peg at the intermediate stage of making the tibial tray of FIGS. 1-4.

The process for making the tibial tray of FIGS. 1-4 can be described with reference to FIGS. 7-17. The second surface 28 of the solid metal base 24 may be coated with porous metal to form the porous metal coating 57 prior to the remaining steps of the process. As shown in FIG. 14, pegs 30A, 32A, 34A, 36A, are inserted into the openings 104, 106, 104A, 106A in the support surface 26 of the base 24 by inserting the shaft 78 (shown in FIG. 14 with respect to peg 34A) first and moving the peg distally until the tapered surface 84 of the head 76 rests against the tapered internal wall 70, 92 of the solid metal base 24 and the distal end of the shaft 78 is exposed beyond the level of the porous coating 57.

Next, the plugs 120, 120A, 120B, 120C are inserted into each of the holes 104, 104A, 106, 106A as shown in FIG. 16. The plugs 120, 120A, 120B, 120C are pressed into the cylindrical chamber 112 until the second cylindrical portion 130 is pressed against the top flat surface 82 of the head 76 of the peg. Because of the dimensions of the cylindrical chamber 112 and the first cylindrical portion 128 of the plug 120, the plug is held in place by the press-fit connection. When inserting the plugs, it may be desirable to press the plug against the head 76 of the peg with enough force to compress the peg. Some permanent or plastic deformation of the head 76 of the peg may occur during assembly. In addition to ensuring a press-fit, it may be desirable to compress the head of the peg sufficiently to overcome the effects of any variation in the dimensions of the heads 76 that might otherwise cause a loose fit.

As shown in FIG. 17, the dimensions of the second cylindrical portion 130 of the plug 120 and the cylindrical chamber 112 allow the plug to be fully inserted without interference from the internal wall 70.

Standard manufacturing equipment, such as an arbor press, may be used to press the pegs and the plugs into the desired positions.

The plugs 120, 120A, 120B, 120C may then be fixed to the solid metal base 24. Illustratively, the plugs 120, 120A, 120B, 120C may be fixed to the solid metal base by welding the plugs and base together along the junctions of the plugs and the base. For example, circular weld 88 may be formed along the wall 126 of the first cylindrical portion 128 of the plugs 120, 120A, 120B, 120C. In addition, welds may be formed along the junctures of the anterior buttress 59 and the plugs 120, 120A. Illustratively, laser welding may be used to form all of the welds.

Next, any undesirable portion of the solid metal plugs 120, 120A, 120B, 120C extending beyond the first solid metal surface 26 of the base 24 may be removed. For the plugs 120B and 120C shown in FIG. 16, any portion of the plugs above the level of the surface 26 may be considered undesirable and removed. For the anterior plugs 120, 120A, the exposed portions of the plugs may be used to form part of the anterior buttress 59. Thus, parts of the anterior plugs 120, 120A would be removed to make a portion level with the mounting surface 26, parts would be removed to make a portion level with the proximal surface of the anterior buttress 59 and parts would be removed to define the contour of the posterior-facing surface of the anterior buttress 59. The removal of undesirable portions of the plugs 120, 120A, 120B, 120C may be accomplished through standard manufacturing processes, such as machining. As part of the removal process, any excess material at any weld lines may be removed as well. Selected surfaces of the tray 14 may be polished as well, if desired.

The end result of this process is the tibial tray 14 shown in FIGS. 1-4, where the porous metal pegs 30, 30A, 32, 32A, 34, 34A, 36, 36A are mechanically, but not metallurgically, fixed to the solid metal base 24. In the final product, the heads 76 of all the pegs 30, 30A, 32, 32A, 34, 34A, 36, 36A are completely covered (that is, no part of the head of any peg is exposed from the mounting surface 26) by solid metal and all of the pegs are held firmly in place by the plugs 120 and internal walls 70, 92. It should be understood that the process described above may also be used to fix pegs to the distal femoral component, such as peg 39 in femoral component 10 of FIG. 1. Moreover, it should be understood that the process described may be used to fix other structures to these components (such as a stem in a mobile bearing tibial tray), and to fix pegs and other structures to other orthopaedic implant components, such as prosthetic hip systems, prosthetic shoulder systems and orthopaedic spine systems.

The components may be dimensioned to allow for an interference fit of the head 76 of the peg 34A against the wall 70. Engineering analysis, such as finite element analysis, may be used to optimize compression of the pegs during assembly.

If the tibial tray is a mobile bearing, and more particularly, a rotating platform tray, the process described above may be used, except there would be no anterior buttress 59. In a rotating platform tray, the peg and plug assemblies would be similar to those for the illustrated posterior pegs 32A, 36A and plugs 120B, 120C (see FIGS. 14 and 16).

To use the system of the present invention, the surgeon would prepare the distal femur and proximal tibia to receive the bone implants 12, 14 using conventional techniques and implant the tibial tray and femoral component using conventional techniques for cementless components. The tibial bearing 16 is typically assembled with the tibial tray 14 after the tray 14 has been implanted.

After implantation, the pegs 30, 30A, 32, 32A, 34, 34A, 36, 36A stabilize the tibial tray 14 and bone will grow into the porous metal coating 57 on the distal surface 28 and into the shafts 78 of the pegs 30, 30A, 32, 32A, 34, 34A, 36, 36A. Similar bone ingrowth would be expected for the femoral component 10. If the pegs are made with smoother distal ends 40, 42, 44, 46, bone will not, however, grow or grow as vigorously into the smoother free ends.

If the exposed peripheral surface of the porous coating 57 is smooth, no soft tissue irritation should occur after the component is implanted.

If it becomes necessary to remove the tibial tray 14 or femoral component 12, the surgeon may cut along a distal plane at the interface of the porous coating 57 and the bone to sever the connection between the patient's bone and the tibial tray platform at the interface. If the pegs 30, 30A, 32, 32A, 34, 34A, 36, 36A consist of porous metal foam across their entire thicknesses along this distal plane, the surgeon may also cut through all of the pegs 30, 30A, 32, 32A, 34, 34A, 36, 36A along this distal plane using a bone saw. Thus, the entire tibial platform may be readily removed with a bone saw. Such a result is generally not possible with pegs and stems made of solid titanium or cobalt chrome alloy, since bone saws cannot generally cut through solid metal. To remove the pegs 30, 30A, 32, 32A, 34, 34A, 36, 36A, the surgeon may then cut around the outer perimeter of each peg 30, 30A, 32, 32A, 34, 34A, 36, 36A to sever the connection between the bone and the pegs 30, 30A, 32, 32A, 34, 34A, 36, 36A. Such cuts around the perimeters may be made, for example, through use of a trephine saw. Each peg 30, 30A, 32, 32A, 34, 34A, 36, 36A may then be readily removed. Notably, if the free ends of the pegs are smooth, little or no bone ingrowth will have occurred at the ends of the pegs, so the removal of the pegs should be made easier.

Thus, the present invention provides a knee prosthesis with a tibial implant component and femoral component suitable for optimized cementless fixation. Moreover, the implant components can be readily removed from the bone in revision surgery to conserve native bone.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, the number and configurations of the pegs may be varied. For a tibial tray, for example, the tray could also include a central stem. Although the illustrated tibial trays have four pegs, fewer pegs may be acceptable. In addition, the heads of the pegs and/or the plugs may be noncircular and, for example, may have a square cross section, and the holes in the base correspondingly sized and shaped. In addition, it also would be possible to attach the plug to the peg, such as by a sintering process, prior to positioning this plug/peg assembly into the hole of the base and then welding the plug to the base as previously described.

Figure 18:
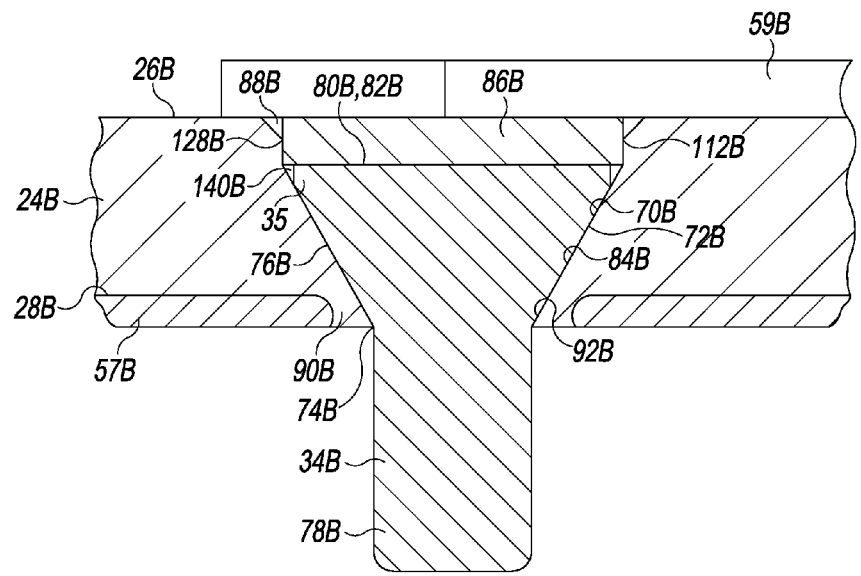
FIG. 18 is a view similar to FIG. 4, illustrating an alternative embodiment of the invention.
Figure 19:
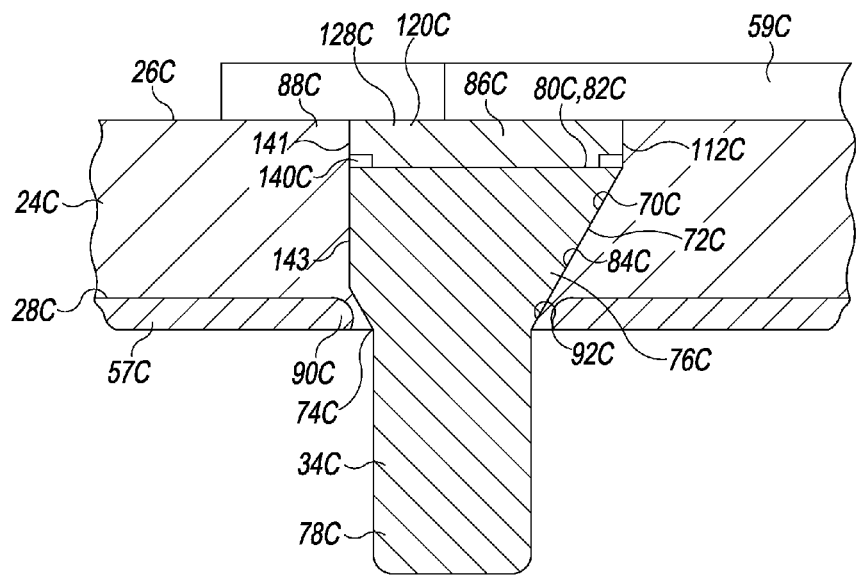
FIG. 19 is a view similar to FIG. 4, illustrating another alternative embodiment of the invention.
Figure 20:
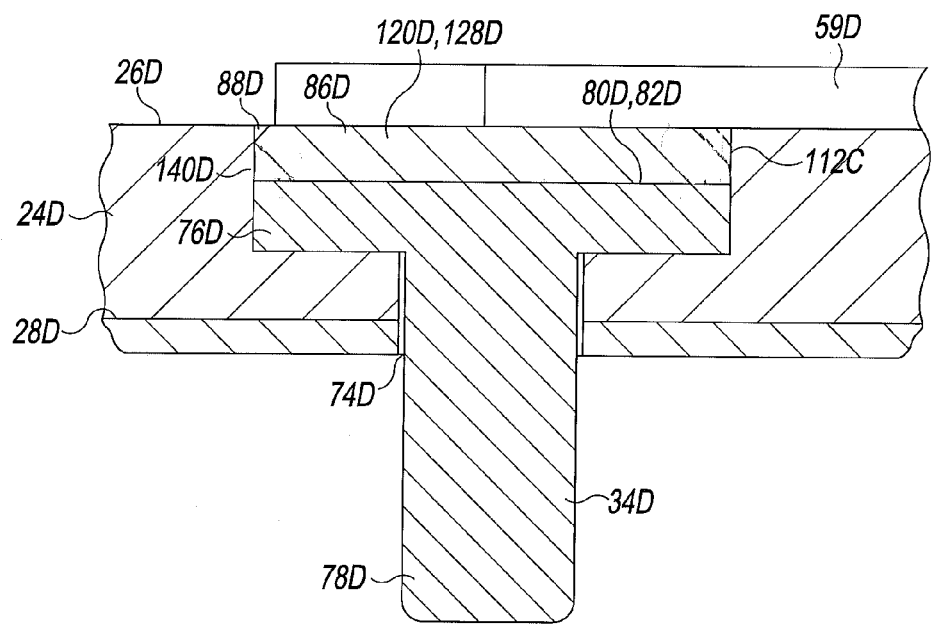
FIG. 20 is a view similar to FIG. 4, illustrating another alternative embodiment of the invention.

Some additional alternative embodiments are illustrated in FIGS. 18-20. In the embodiment of FIG. 18, parts similar to those described above for the first embodiment are labeled with the same reference numbers, followed by the letter "B". In the embodiment of FIG. 19, parts similar to those described above for the first embodiment are labeled with the same reference numbers, followed by the letter "C". In the embodiment of FIG. 20, parts similar to those described above for the first embodiment are labeled with the same reference numbers, followed by the letter "D". It should be understood that the above description of the components apply as well to the embodiments illustrated in FIGS. 18-20 unless distinguished in the following description.

In the embodiment of FIG. 18, the plug 120B has a single cylindrical portion 128B of constant diameter. The head 76B of the peg 34B has a proximal cylindrical portion 35 adjacent to a frusto-conical portion 37 defined by surface 84B. The diameter of the cylindrical portion 35 of the head 76B is less than the diameter of the cylindrical chamber 112B in the base 24B. The annular gap 140B is adjacent to and level with the top surface 82B of the peg 34B in the embodiment of FIG. 18. In this embodiment, the free end 80B of the head 76B of the peg 34B extends proximally beyond the junction of the cylindrical chamber 112B and chamfered chamber 72B.

In the embodiment of FIG. 19, the plug 120C and the head 76C of the peg 34C include anti-rotation flats 141, 143.

In the embodiment of FIG. 20, the head 76D of the peg 34D is cylindrical and the plug 120D has a single cylindrical portion 128D of constant diameter. The base 24D has a single cylindrical chamber 112D defined by a side wall 147 and bottom wall 147. In this embodiment, the bottom wall 147 is substantially parallel to the mounting surface 26D and to the top surface 82D of the peg 34D.

It should be appreciated that other shapes of the head 76 of the peg 34 and the plug 120 may be used, along with other shapes of chambers in the base 24 to receive the head 76 and plug 120. For example, the head of the peg could be stepped to mate with and be received within a counterbore in the base 24. The plug may also have a tapered, frusto-conical shape instead of a right cylinder shape if desired.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

We claim:

1. An orthopaedic prosthesis comprising:
   a first component comprising a solid metal portion and a porous metal portion,
   the solid metal portion including a first solid metal surface and a second solid metal surface spaced from the first solid metal surface,
   the solid metal portion having an internal wall extending from the second solid metal surface toward the first solid metal,
   the internal wall being tapered to have a minimum internal diameter furthest from the first solid metal surface and to define an internal chamfered chamber,
   the second solid metal surface having an opening at the junction of the internal wall and the second solid metal surface;
   the porous metal portion including a peg having a porous metal head and a porous metal shaft,
   the head of the peg having a first free end and a tapered wall extending from the junction of the head and the shaft toward the first free end,
   the peg having a maximum outer diameter at the first free end and a smaller outer diameter at the junction of the head and the shaft,
   at least a substantial part of the head of the peg being received within the chamfered chamber in the solid metal portion between the first solid metal surface and the second solid metal surface, a portion of the peg extending outward through the opening in the second solid metal surface;

wherein the solid metal portion includes a plug that extends from the first solid metal surface to the head of the peg and covers the head of the peg;

wherein a weld connects the plug to another part of the solid metal portion so that the first solid metal surface, weld and plug define a continuous solid metal surface; and wherein there is no metallurgical bonding between the peg and the second solid metal surface of the solid metal portion.

2. The orthopaedic prosthesis of claim 1 wherein there is no metallurgical bonding between the peg and the solid metal portion.

3. The orthopaedic prosthesis of claim 1 wherein the solid metal portion and porous metal portion comprise different metals.

4. The orthopaedic prosthesis of claim 1 wherein the solid metal portion includes cobalt and the porous metal portion includes titanium.

5. The orthopaedic prosthesis of claim 4 wherein the solid metal portion comprises an alloy of cobalt, chromium and molybdenum and the porous metal portion comprises titanium metal foam.

6. The orthopaedic prosthesis of claim 1 wherein:
the first component comprises a distal femoral implant component having articular surfaces and bone-facing surfaces; and
the first surface comprises one of the articular surfaces and the second surface comprises one of the bone-facing surfaces.

7. The orthopaedic prosthesis of claim 6 further comprising a bearing having articular surfaces to receive the articular surfaces of the distal femoral implant component.

8. The orthopaedic prosthesis of claim 7 wherein the bearing has a mounting surface spaced from the articular surfaces of the bearing and the prosthesis further comprises a tibial tray having a support surface to accept the mounting surface of the bearing.

9. The orthopaedic prosthesis of claim 8 wherein:
the mounting surface of the bearing and support surface of the tibial tray have complementary structures to fix the bearing to the tibial tray;
the complementary structures include a solid metal anterior buttress extending proximally from and being continuous with the support surface of the tray; and
a portion of the anterior buttress overlies at least a portion of the head of the peg with solid metal extending between the anterior buttress and the head of the peg.

10. The orthopaedic prosthesis of claim 1 wherein the solid metal portion includes a solid metal annulus surrounding the peg, the solid metal annulus being continuous with and extending from the second solid metal surface of the solid metal portion of the first component.

11. The orthopaedic prosthesis of claim 10 wherein there is no metallurgical bond between the solid metal annulus and the peg.

12. The orthopaedic prosthesis of claim 11 wherein the metal annulus extends about 1 mm out from the surface of the peg.

13. The orthopaedic prosthesis of claim 11 wherein the metal annulus has a tapered inner wall continuous with the tapered inner wall of the chamfered chamber so that the chamfered chamber extends beyond the level of the second solid metal surface.

14. The orthopaedic prosthesis of claim 10 wherein the porous metal portion includes a layer of porous metal metallurgically bonded to the second solid metal surface.

15. The orthopaedic prosthesis of claim 1 wherein there is an annular gap in the solid metal portion adjacent to the first free end of the head of the peg.

16. The orthopaedic prosthesis of claim 1 wherein the chamfered chamber has a central longitudinal axis and wherein the internal wall of the chamfered chamber defines an angle of about 40 degrees with the central longitudinal axis.

17. The orthopaedic prosthesis of claim 1 wherein the solid metal portion of the first component has a thickness of less than 5 mm between the first solid metal surface and the second solid metal surface.

18. A method of making a joint prosthesis from a solid metal base, a porous metal peg and a solid metal plug, wherein:
the solid metal base includes a first solid metal surface and a second solid metal surface spaced from the first solid metal surface, a hole in the first solid metal surface, a hole in the second solid metal surface and an internal wall extending between and defining the holes, the internal wall having a tapered portion and a cylindrical portion, the tapered portion having a minimum internal diameter at the second solid metal surface and a maximum outer diameter at a position between the first solid metal surface and the second solid metal surface, the cylindrical portion of the internal wall extending from the tapered portion to the first solid metal surface, the tapered portion of the internal wall defining a chamfered chamber and the cylindrical portion defining a cylindrical chamber;
the peg includes a head and a shaft, the head having a first free end, an end surface at the first free end and a tapered wall extending from the first free end to the junction of the head and the shaft, the peg having a maximum outer diameter at the first free end and a smaller outer diameter at the junction of the head and the shaft;
the plug includes a first solid metal surface, a second solid metal surface spaced from the first solid metal surface and a side wall extending from the first solid metal surface toward the second solid metal surface;
the method comprising:
positioning the peg with the tapered wall of the head bearing against the tapered portion of the internal wall and with the shaft of the peg extending outwardly past the second solid metal surface of the solid metal base, wherein the end surface of the head of the peg does not extend beyond the junction of the chamfered chamber and cylindrical chamber in the solid metal base;
press-fitting the plug into the cylindrical chamber in the solid metal base with the second solid metal surface of the plug bearing against the end surface of the head of the peg and with the side wall of the plug engaging the cylindrical portion of the internal wall defining the cylindrical chamber;
welding the solid metal plug to the first solid metal surface of the solid metal base; and
removing any undesirable portion of the solid metal plug extending beyond the first solid metal surface of the base.

19. The method of claim 18 wherein:
the cylindrical chamber of the solid metal base has an internal diameter;
the first solid metal surface of the plug has an outer diameter, the first solid metal surface of the plug and the side wall of the plug defining a first cylindrical portion;
the second solid metal surface of the plug has an outer diameter, the second solid metal surface of the plug and the side wall of the plug defining a second cylindrical portion;
the outer diameter of the first cylindrical portion of the plug is greater than the outer diameter of the second cylindrical portion of the plug; and
the inner diameter of the cylindrical chamber and the outer diameter of the first cylindrical portion of the plug are dimensioned to allow for the first cylindrical portion of the plug to be press-fit into the cylindrical chamber.

20. The method of claim 19 wherein there is no contact between the second cylindrical portion of the plug and the internal wall of the solid metal base after the first cylindrical portion of the plug has been press-fit into the cylindrical chamber.

21. The method of claim 19 wherein:
the first cylindrical portion of the plug has an axial length;
the cylindrical chamber of the solid metal base has an axial length; and
the axial length of the first cylindrical portion of the plug is greater than the axial length of the cylindrical chamber of the solid metal base.

22. The method of claim 21 wherein:
the solid metal base includes an anterior buttress extending outward from the first solid metal surface to a height;
the axial length of the first cylindrical portion of the plug is great enough to extend to the height of the anterior buttress so that a portion of the first cylindrical portion of the plug is exposed above the first solid metal surface of the solid metal base;
the method includes:
fixing the first cylindrical portion of the plug to the anterior buttress;
removing a portion of the first cylindrical portion of the plug after welding so that a portion of the first cylindrical portion of the plug defines a portion of the anterior buttress.

23. The method of claim 18 wherein the second solid metal surface of the solid metal base includes a solid metal annulus surrounding the hole in the second solid metal surface and extending outward from the second solid metal surface to an outer surface.

24. The method of claim 23 wherein the axial distance from a plane at the outer surface of the annulus to a plane through the junction of the cylindrical chamber and chamfered chamber is substantially the same as the axial length of the head of the peg.

25. The method of claim 23 wherein the outer diameter of the annulus is no more than 2 mm greater than the inner diameter of the annulus.

26. The method of claim 25 further comprising the step of coating the second solid metal surface of the solid metal base with porous metal around the annulus and sintering the porous metal coating to the solid metal base.

27. The method of claim 26 wherein the outer surface of the annulus and the exposed surface of the porous metal coating are substantially co-planar.

28. The method of claim 18 wherein the step of press-fitting the plug into the cylindrical chamber compresses the head of the peg.

29. The method of claim 18 wherein the peg comprises a metal foam containing titanium, the solid metal base comprises alloy containing cobalt and the solid metal plug comprises an alloy containing cobalt.

30. The method of claim 18 further comprising the step of coating the second solid metal surface of the solid metal base with porous metal and sintering the porous metal coating to the solid metal base.

31. The method of claim 18 wherein:
the solid metal base includes a plurality of cylindrical chambers and a plurality of chamfered chambers;
a plurality of porous metal pegs are provided, and one porous metal peg is positioned within each chamfered chamber;
a plurality of solid metal plugs are provided, and one solid metal plug is press-fit into each cylindrical chamber;
each solid metal plug is welded to the solid metal base; and
any undesirable excess of any plug extending beyond the first solid metal surface of the base is removed.

32. The method of claim 18 wherein the joint prosthesis comprises a prosthetic knee implant having a proximal tibial implant component, a distal femoral implant component and a bearing.

33. The method of claim 18 wherein the solid metal base is part of the proximal tibial component and the first solid metal surface defines a support surface for the bearing.

34. The method of claim 33 further comprising the step of polishing the first solid metal surface after the step of removing any portion of the solid metal plug extending beyond the first solid metal surface of the base.

35. An orthopaedic prosthesis comprising:
a first component comprising a solid portion and a porous portion,
the solid portion including a first solid surface and a second solid surface spaced from the first solid surface,
the solid portion having an internal wall extending from the second solid surface toward the first solid surface and defining a chamber;
the second solid surface having an opening at the junction of the internal wall and the second solid surface;
the porous portion including a peg having a head and a shaft,
at least a substantial part of the head of the peg being received within the chamber in the solid portion between the first solid surface and the second solid surface,
a portion of the peg extending outward through the opening in the second solid surface;
wherein the solid portion includes a plug that bears against the head of the peg and is welded to another part of the solid portion so that the solid portion defines a continuous solid surface that covers the head of the peg; and
wherein the peg and the second solid surface of the solid portion are not bonded together.

36. The orthopaedic prosthesis of claim 35 wherein the solid portion of the first component comprises metal.

37. The orthopaedic prosthesis of claim 35 wherein the peg comprises porous metal.

38. The orthopaedic prosthesis of claim 35 wherein at least a part of the chamber in the solid portion is frusto-conical in shape.

39. The orthopaedic prosthesis of claim 35 wherein the head of the peg is frusto-conical in shape.

40. A method of making a joint prosthesis from a solid base, a porous peg and a solid plug, wherein:
the solid base includes a first solid surface and a second solid surface spaced from the first solid surface, a hole in the first solid surface, a hole in the second solid surface and an internal wall extending between and the holes and defining a chamber;

the peg includes a head and a shaft, the head having a first free end, the peg having a maximum outer diameter at the first free end and a smaller outer diameter at the junction of the head and the shaft;

the plug includes a first solid surface, a second solid surface spaced from the first solid surface and a side wall extending from the first solid surface toward the second solid surface;

the method comprising:

positioning the peg in the chamber in the solid base;

press-fitting the plug into the chamber in the solid base with the second solid surface of the plug bearing against the end surface of the head of the peg;

welding the solid plug to the first solid surface of the solid base; and removing any undesirable portion of the solid plug extending beyond the first solid surface of the base.

41. The method of claim 40 wherein the solid base comprises metal and the plug comprises metal.

42. The method of claim 40 wherein the peg comprises porous metal.

43. The method of claim 40 wherein at least part of the chamber and the head of the peg are frusto-conical in shape.

\* \* \* \* \*